(12) United States Patent
Kozlenko (10) Patent No.: US 8,617,544 B2
(45) Date of Patent: Dec. 31, 2013

(54) COMPOSITIONS AND METHODS FOR CONTROLLING LIPID METABOLISM

(76) Inventor: Richard L. Kozlenko, San Rafael, CA (US)

( * ) Notice: Subject to any disclaimer, the term of this patent is extended or adjusted under 35 U.S.C. 154(b) by 706 days.

(21) Appl. No.: 12/464,551

(22) Filed: May 12, 2009

(65) Prior Publication Data
US 2009/0291071 A1    Nov. 26, 2009

Related U.S. Application Data

(63) Continuation of application No. 11/799,213, filed on May 1, 2007, now abandoned.

(51) Int. Cl.
*A61K 35/00*    (2006.01)
*A61K 9/00*    (2006.01)
*A61K 47/00*    (2006.01)
*A61K 9/20*    (2006.01)

(52) U.S. Cl.
USPC ............ 424/115; 424/400; 424/439; 424/464

(58) Field of Classification Search
USPC ................................. 424/115, 400, 439, 464
See application file for complete search history.

(56) References Cited

U.S. PATENT DOCUMENTS

| | | | |
|---|---|---|---|
| 5,258,192 A * | 11/1993 | Kusano | 426/133 |
| 5,487,894 A | 1/1996 | Kovacs | |
| 5,648,377 A | 7/1997 | Bombardelli et al. | |
| 5,928,646 A | 7/1999 | Nkiliza | |
| 5,994,413 A | 11/1999 | Tanabe et al. | |
| 6,099,854 A | 8/2000 | Howard et al. | |
| 6,165,539 A | 12/2000 | Erasmus et al. | |
| 6,203,797 B1 | 3/2001 | Perry | |
| 6,391,864 B1 | 5/2002 | Stone | |
| 6,437,004 B1 | 8/2002 | Perricone | |
| 6,465,018 B1 | 10/2002 | Tuttle | |
| 6,485,772 B1 | 11/2002 | Tanaka et al. | |
| 6,638,545 B1 | 10/2003 | Rombi | |
| 6,642,277 B1 | 11/2003 | Howard et al. | |
| 6,753,019 B1 | 6/2004 | Lang et al. | |
| 6,979,457 B2 | 12/2005 | Watson et al. | |
| 6,986,906 B2 | 1/2006 | Selzer et al. | |
| 7,041,699 B2 | 5/2006 | Netke et al. | |
| 7,115,283 B2 | 10/2006 | Chang | |
| 7,118,688 B2 | 10/2006 | Mora-Gutierrez et al. | |
| 7,153,503 B1 | 12/2006 | Henderson | |
| 7,172,773 B2 | 2/2007 | Watson | |
| 7,192,612 B2 | 3/2007 | Morré et al. | |
| 2005/0208197 A1 | 9/2005 | Suwa et al. | |

OTHER PUBLICATIONS

The Justice.org, obtained online at: http://www.thejustice.org/arts/local-brewery-delivers-grand-tastes-1.2351367, downloaded on Sep. 17, 2012, published online: Oct. 26, 2010.*
Revilla et al., J. Agric. Food. Chem., 1998, 45, 4592-4597.*
MacPhillamy, Plant Science Bulletin, 1963, 9(2), 1-15.*
Phillipson, Phytotherapy Research, 1999, 13, 2-8.*
Raskin et al., Current Pharmacuetical Design, 2004, 10, 3419-3429.*
Hay et al., Proceedings of the American Society of Brewing Chemists, 1962, 127-131.*
Sinatra et al., Anti-Ageing Therapeutics, 2006, Chapter 4: Fire in the Heart:New Developments in Diagnosis, Prevention and Treatment of Cardiovascular Disease. Obtained from : http://www.worldhealth.net/pdf/bookstore/thera6_ch4.pdf. pp. 27-45.
Fantozzi et al., Food Scieence and Technology, 1998, 31 (3), 221-227.
Yamamoto et al., Journal of Chemical Engineering of Japan, 2006, 39(9), 956-962).

* cited by examiner

*Primary Examiner* — Abigail Fisher (57) ABSTRACT

The present invention provides a neutraceutical formulation having unexpected optimizing effects on the release of various gastric hormones and which acts unexpectedly and synergistically to inhibit various metabolic reactions such as oxidation and glycation of lipoproteins, especially LDLs. An enhancement in the release of gastric hormones optimizes the release of various gastric juices, gastric enzymes, and endocrine secretion levels of hormones that have key roles in the metabolism, digestion, assimilation of caloric and non-caloric nutrients, the storage of body fats, and appetite satiety. The present composition has further effects as an antioxidant formulation and as an enhancer and stabilizer of the activity of other antioxidants.

5 Claims, 4 Drawing Sheets

COMPOSITIONS AND METHODS FOR CONTROLLING LIPID METABOLISM

CROSS-REFERENCE TO RELATED APPLICATIONS

The present application is a continuation of U.S. Ser. No. 11/799,213 filed May 1, 2007 now abandoned, the entirety of which is hereby expressly incorporated herein by reference.

STATEMENT REGARDING FEDERALLY SPONSORED RESEARCH OR DEVELOPMENT

Not applicable.

BACKGROUND OF THE INVENTION

The present invention is directed, but not limited to, compositions which affect digestion in the gastrointestinal system and which have antioxidative effects, and more particularly which unexpectedly enhance lipid, protein, and carbohydrate metabolism in the gastrointestinal tract and unexpectedly enhance the effects of other antioxidants.

The stomach, pancreas, liver, gallbladder and small intestine are all involved in various roles concerning the process of digestion and assimilation, fat, protein and carbohydrate metabolism, the stabilization of blood sugar, and the storage of body fats. These processes are principally regulated by four interrelating digestive hormones, and two endocrine hormones. The four digestive hormones include gastrin, secretin, cholecystokinin and enterogastrone. The two counterbalancing endocrine hormones, which profoundly effect blood sugar and fat storage, are insulin and glucagon, both of which are from the pancreas and are directly stimulated by the gastric hormones that are enhanced by the composition of the present invention.

Gastrin is released by the stomach lining in response to the presence of food and stimulates the production of gastric juices. It is the primary regulator of digestion and the digestion sequence. Also, gastrin causes the esophageal sphincter to contract reducing the gastroesophageal reflux or heartburn. Gastrin also stimulates secretin release from the duodenum. The metabolic effects of gastrin is that it strongly stimulates release of insulin and weakly stimulates glucagon secretion.

The acidic chyme from the stomach stimulates release of secretin as it enters the duodenum. The secretin signals the release of bicarbonate which neutralizes stomach acid as it enters the intestinal environment. Glucagon has a sequence of 14 amino acids in common with secretin, a 27-amino acid oligopeptide. These two substances share many similar properties in their metabolic effects. Both help stimulate release of insulin (insulin counteracts glucagon). Both enhance lipolysis from adipose tissue by the stimulation of the enzyme, adenyl-cyclase. Secretin is actually stronger than glucagon in this effect. Glucagon raises blood sugar, secretin does not, and insulin lowers blood sugar.

A third crucial hormone produced by the duodenum is cholecystokinin (CCK). CCK causes the gallbladder to contract and release bile into the small intestines. Bile helps in the emulsification and absorption of fats and lipids. CCK also triggers the release of pancreatic enzymes, which break down proteins, lipids and carbohydrates in the small intestine. Most investigators agree that CCK is linked in its effects to the hypothalamus and related to appetite regulation and feelings of satiety.

If the chyme leaving the stomach is particularly rich in fats, the duodenum releases enterogastrone, which inhibits the peristalsis in the stomach, thereby slowing down the entry of food into the small intestines.

Atherosclerosis is a condition wherein the walls of the arteries are damaged and narrowed by deposits of plaque (cholesterol and other fatty substances, calcium, fibrin, and cellular wastes), eventually blocking off the flow of blood. Plaque deposits can result in bleeding (hemorrhage) or formation of a blood clot (thrombus). When hemorrhage or thrombus blocks the flow of blood through the entire artery, the heart attack or a stroke occurs. High blood levels of cholesterol, particularly the cholesterol carried by low density lipoprotein (LDL) are associated with an increased risk of atherosclerosis.

Normal LDL in plasma is not oxidized. Oxidation of LDL cholesterol is believed to contribute to the development of atherosclerosis and cardiovascular disease in general.

Dietary supplements of antioxidants such as Vitamin E are thought by many to reduce oxidation of LDL.

An objective of the present invention therefore is to improve control of the appetite and function of the gastrointestinal system and further to provide antioxidant effects.

DETAILED DESCRIPTION OF THE INVENTION

The present invention provides a neutraceutical formulation having unexpected and optimizing effects on the release of various gastric hormones and which act unexpectedly and synergistically to inhibit various metabolic reactions such as oxidation and glycation. An enhancement in the release of gastric hormones optimizes the release of various gastric juices, gastric enzymes, and endocrine secretion levels of hormones that have key roles in the metabolism, digestion, assimilation of caloric and non-caloric nutrients, the storage of body fats, and appetite satiety. The present composition has further effects as an antioxidant formulation and as an enhancer and stabilizer of the activity of other antioxidants.

The composition of the present invention has one of its effects in stimulation lipid digestion and enhancing feelings of satiety and thus reducing a subject's appetite. Without wishing to be bound by theory, it is believed the composition has its effects in this manner by stimulation the secretion of CCK and other gastrointestinal hormones, and thus secretion of bile and pancreatic enzymes which enhance the digestion of lipids, carbohydrates, and proteins in the small intestine. CDK further enhances feelings of satiety by action on the hypothalamus to induce a sense of fullness, thus decreasing one's appetite. By providing the present composition as a non-alcoholic, dried form, the beneficial effects of the constituents of beer are obtained without the deleterious effects of alcohol and without the calories contributed by the alcohol originally present in the beer.

In one embodiment, the present invention is a solid composition which comprises from 1% to 100% dried beer solids.

In a preferred embodiment, the dried beer composition of the present invention comprises a dry solid material having 10 mg to 5 g per dose of evaporated beer (i.e., substantially absent ethanol and water) wherein the dry beer solids comprise 1% to 100% (by weight percentage) of the composition, and may optionally comprise D-ribose, alone, or with other ingredients described herein at concentrations of 1 to 2000 mg per dosage.

The composition may further comprise additional dry solids obtained from the beer brewing waste stream such as hop components (wherein the beer brewing waste stream is defined herein as any material derived from the beer wort or other component obtained from the beer mash after fermentation of the beer mash). Such beer waste stream dry solids may comprise from 0.001% to 90% of the dried beer composition, or from 1 to 10,000 ppm per dose, for example. The beer waste stream dry solids may contain or be enriched with beer proteins, beta glucans, vitamins, antioxidants, xanthohumol, or other biologically-active components found in beer and hops.

As noted above, the present composition has antioxidant effects, and anti-glycation effects and effects in enhancing and stabilizing the capabilities of other antioxidants. Thus, the dried beer composition of the present invention may be further enriched with one or more antioxidant components comprising phenols including flavonols, flavonoids, and polyphenols, for example as described below.

Antioxidants which can be added to the dried beer composition include, but are not limited to, ascorbic acid (Vitamin C), alpha-tocopherol and derivatives (Vitamin E and the Vitamin E family); extracts of Hawthorn (*Crataegus*) flower buds, flowers, young leaves, green fruits; proanthocyanidins such as procyanidin B2; flavonol glycosides such as hyperoside; carotenoids such as beta-carotene, alpha-carotene, lycopene, ubidecarenone, oxygenated carotenoids (including lutein, zeaxanthin, canthaxanthin, beta-cryptoxanthin, capsanthin, and other xanthophylls); grape juice and grape seed extract; apple extract; cranberry extract; heliant (sunflower seed extract); olive extract (including the polyphenols oleoeuropeine and hydroxy tyrosol); green or black tea extracts; curcumin, bilberry extract; cis and trans resveratrol; cocoa bean extract, citrus bioflavonoids; rosemary extract; elderberry extract; extracts of ripe and unripe fruit of the Rosaceae (including apple, pear, peach, plum, and apricot); and extracts of *Potentilla* species.

Other polyphenols which can be used as additional components of the dried beer solid composition include, but are not limited to, catechin, epicatechin, gallocatechin, gallocatechin gallate, epigallocatechin, epicatechin gallate, epidallocatechin gallate, and salts thereof, anthongandiding, oligomeric proanthocyanidins or proanthanols, caffeic acid derivatives, p-coumaric acid derivatives flavan-3-ols (e.g., catechines), flavonols (e.g., quercetin glycosides), dihydrochalcones (phloretin glycosides, such as phloridzin), condensed tannins, caffeic acid, caffeic acid esters, p-coumaric acid, p-coumaric acid esters, phloretin, phloretin glycosides, quercetin, quercitin glycosides, catechin, epicatechin, and condensed tannins; flavanones; catechol; epicatechol; kaempferol, myricetin, and flavonol glycosides of glucose, galactose, arabinose, and rhamnose, for example, and methylated, sulfated, and malonylated flavonols, and gallic acid, procyanin dimers, caftaric acid, coutaric acid, O-coumaric acid, myricetin glycosides, myricetin, delphinidin glycosides, peonidin glycosides, petunidin glycosides, malvidin glycosides, polymeric anthocyanins, delphinidin diglucosides, cyanidin diglucosides, peonidin diglucosides, petunidin diglucosides, and malvidin diglucosides. These antioxidants preferably comprise 1 to 2000 mg per dosage.

Other ingredients which, though not critical to the function of the composition, may be deemed as helpful in assisting in its roles of lipid metabolism and management which may be added to the composition include, but are not limited to, varying amounts of soluble fibers or gums from any sources, vitamins, minerals, and amino acids or proteins, carbohydrates, sugar alcohols, enzymes, digestants and acidulants, and probiotics, wherein preferred levels are from 1 mg-2000 mg per dosage.

The compositions of this invention may contain the dehydrated beer solids and other optional components with a solid or liquid pharmaceutically acceptable nontoxic carrier or vehicle. Such pharmaceutical carriers or vehicles include, but are not limited to, sterile liquids, such as water and oils, including those of petroleum, animal, vegetable or synthetic origin, such as peanut oil, soybean oil, mineral oil, sesame oil and the like. Suitable such excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene glycol, and inert polymers and the like. These compositions can take the form of tablets, pills, capsules, powders, sustained-release formulations and the like. Suitable pharmaceutical carriers are described in "Remington's Pharmaceutical Sciences", latest edition. Such compositions will thus contain an effective amount of the dried beer solids together with a suitable amount of the carrier or vehicle so as to provide the form for proper administration to the subject.

The compositions of this invention can further include a filler, flavoring agent, binder, mineral, and excipients and mixtures thereof. Tablets can be coated with a film and/or color layer for protection and color as is known in the art. These additives are conventional components of such formulations.

The unexpected and unobvious benefits offered by the present invention include, but are not limited to: (1) increasing lipolysis from fat cells; (2) enhancing feelings of satiety, and thus, better appetite regulation by stimulating GI hormones which control appetite, blood sugar, and absorption of nutrients; (3) stimulation of endocrine hormones important in fat storage and energy metabolism; (4) stabilizing antioxidants and reducing the oxidative conversion and/or glycation of blood lipoproteins such as LDL-cholesterol, thereby contributing to the reduction of atherosclerosis; (5) reduction of blood sugar spiking that is directly and indirectly related to sugar to fat metabolism and appetite stimulation; (6) reducing the proxidant effects of simple sugars on the oxidation of essential lipid stabilizing antioxidants; (7) synergism with antioxidant additives to decrease LDL oxidation and glycation thereby reducing inflammatory conditions and contributing to the reduction of atherosclerosis; and (8) improving lean tissue mass and bone mineralization.

Lean tissues are defined herein as all tissues other than white body fat. Most significantly, lean tissue includes muscle, bones, blood, nerve and organs. Lean tissue enhancement of the present invention involves stimulation of physiological events, as well as ingredients that are favorable to bone mineralization. Novel assay studies of the dried beer component of the invention have determined meaningful levels of xanthohumol and other weak estrogenic-like compounds present that have been related to a protective effect of bone tissues. These compounds are found in the evaporated beer component of the invention, and in greater concentration in the evaporated hop portion of dried brewed beer wastestream which may also comprise a component of the dried beer composition.

Also, the present invention induces acidity and other enhanced gastric events, which creates a favorable environment for the enhanced absorption of important bone and nerve tissue nutrients including calcium, zinc, and various B vitamins, especially vitamin B12.

Also, the dried beer component of the invention and the option to combine it with other soluble fibers and gums and carriers, presents an environment conducive to GI bacteria such as *Lactobacillus acidophilus* and *Bifidobacterium bifidum* and the synthesis of short chain fatty acids (SCFA), which enhance the absorption of bone minerals, such as calcium, silica, and other minerals from the diet.

As noted above, the central ingredient of the present invention is a non-alcoholic, dried composition of concentrated beer solids. Results shown herein demonstrate that the dried beer composition of the present invention has a significant positive synergy with the lipoprotein-stabilizing effects of antioxidants such as Vitamin E and Vitamin C. For example, this study demonstrates that the dried beer composition of the invention, can increase the effectiveness of Vitamin E and other antioxidants in inhibiting LDL oxidation up to 95%.

Studies were conducted to evaluate the biological efficacy of non-alcoholic dry beer solids of the present invention on lipids and antioxidant activity. The present embodiment of beer in the invention demonstrated positive and beneficial lipidemic and antioxidant effects by reducing total cholesterol and triglycerides, and elevating high density lipoprotein (HDL) to total cholesterol ratios. Also, the present dried beer composition unexpectedly enhances antioxidant efficacy by decreasing levels of serum lipid peroxides and by enhancing the stabilization of antioxidants.

When dried beer solids, Heliant, Vitamin E and Vitamin C were combined with glucose or D-ribose, and lipoprotein, glycation of the lipoprotein by glucose and D-ribose was inhibited. Similarly when RBC-Vitamin C or Vitamin E were combined with sorbitol and lipoprotein, glycation of the lipoprotein by sorbitol was inhibited.

As noted above, in a preferred embodiment of the invention, the dried beer composition includes one or more active additives, in particular antioxidants such as polyphenolic compounds. Much data support a role for both low density lipoprotein (LDL) oxidation and glycation in atherosclerosis. Atherosclerosis, in the simplest terms, is the accumulation of low density lipoprotein-cholesterol (LDL-cholesterol), or "bad cholesterol", in arteries resulting in restricted blood flow. In the advanced stages of the disease blood flow may be decrease severely or cease completely resulting in angina (chest pain), a thrombosis (blood clot), and/or myocardial infarction (heart attack). Atherosclerosis is a primary cause of cardiovascular disease (CVD). According to the American Heart Association (2001), on average one person in the U.S. dies every 33 seconds from a cardiovascular illness. Cardiovascular disease is the leading cause of death in the U.S. Oxidation of low density lipoproteins (LDL) induced by free radicals has been hypothesized to play a key role in the atherosclerotic process. Prevention of LDL oxidation thus is a primary focus in reducing the risk of CVD. Glycated LDL is a form of low density lipoprotein with one or more sugar molecules attached thereto and, with oxidized LDL, is known as "the bad cholesterol". While not being bound to any particular theory of operation, it is widely believed that glycation and oxidation of LDLs, such as LDL cholesterol, significantly contribute to cardiovascular disease such as atherosclerosis by causing the LDL-cholesterol molecules to bind to the inner lining of blood vessels causing their occlusion and thus reducing the efficiency of blood flow, and sometimes myocardial infarction or occluded blood vessels.

Because LDLs transport cholesterol to the arteries, increased levels are associated with atherosclerosis, and thus heart attack, stroke and peripheral vascular disease. Increasing evidence has revealed that the concentration and size of the LDL particles more power fully relates to the degree of atherosclerosis progression than the concentration of cholesterol contained within all the LDL particles. The healthiest pattern, though relatively rare, is to have small numbers of large LDL particles and no small particles. Having small LDL particles correlates with much faster growth of atheroma, progression of atherosclerosis and earlier and more severe cardiovascular disease events and death.

LDL is formed as VLDL lipoproteins, which lose triglyceride through the action of lipoprotein lipase (LPL), and become smaller and denser containing a higher proportion of cholesterol. A hereditary form of high LDL is familial hypercholesterolemia (FH). Increased LDL is termed hyperlipoproteinemia type II (after the dated Fredrickson classification).

As noted above, LDL poses a risk for cardiovascular disease when it invades the vascular endothelium and becomes oxidized. A complex set of biochemical reactions regulates the oxidation of LDL, chiefly stimulated by presence of free radicals in the endothelium. Nitric oxide down-regulates this oxidation process catalyzed by L-arginine. Correspondingly when there are high levels of asymmetric dimethylarginine in the endothelium, production of nitric oxide is inhibited and more LDL oxidation occurs.

In coronary atherosclerosis low-density lipoprotein (LDL) cholesterol and cholesterol esters accumulate within a layer of cells beneath the transparent endothelium. On microscopic examination, these cells, called "foam cells", display an abundance of amorphous lipid droplets. The LDL in foam cells differs from native LDL in both surface charge and by the presence of aldehyde-lysine adducts. These modifications may occur as a result of lipid peroxidation, and oxidized LDL is probably involved in the genesis of atherosclerotic plaques. Macrophage cells preferentially take up oxidized LDL, become loaded with lipids, and convert into these foam cells. Foam cells accumulate in fatty streaks, early signs of atherosclerosis. Humans produce auto-antibodies against oxidized LDL, and the levels of such auto-antibodies are higher in patients with atherosclerosis.

The development of an atherosclerotic plaque is thought to be initiated by injury to the vascular endothelium. In response to this injury, monocytes migrate into the subendothelial intima, where they differentiate into tissue macrophages. Lipid peroxidation and modification of LDL may be important early events in the transformation of these tissue macrophages into foam cells. The peroxidation of fatty acids yields specific aldehydic breakdown products that react with lysine residues in LDL and apolipoprotein.

The modified LDL can self-polymerize or can react with mast cell proteoglycan to form aggregates containing 5,000 to 10,000 individual LDL particles. Oxidized LDL is chemotactic for monocytes and functions in their recruitment into the arterial intima, where they differentiate into tissue macrophages. Furthermore, oxidized LDL inhibits migration of macrophages away from the arterial wall. Because macrophages can oxidize LDL, the process can be self-perpetuating.

The uptake of LDL by macrophages appears to occur through three parallel mechanisms. First, unmodified or slightly modified LDL binds to the specific LDL receptor on the macrophage cell surface and is endocytosed. The activity of the macrophage LDL receptor is regulated by intracellular cholesterol content, and it is generally believed that this mechanism prevents foam-cell formation. Second, oxidized LDL is internalized by the macrophage scavenger receptor, which has a broad specificity and is not regulated by cellular cholesterol content. Third, aggregated LDL and large LDL-proteoglycan complexes are directly ingested by phagocytosis. This is a very nonspecific pathway and, again, is not regulated by cellular cholesterol.

Endocytosed cholesterol can be returned to the circulation by esterificiaton and donation to high-density lipoproteins (HDL). The efficient operation of this reverse cholesterol transport blocks atheroma formation, and clinical disease is not manifested. Endocytosed polymeric LDL and LDL-proteoglycan complexes are metabolized slowly within macrophages, and cholesterol from these sources is not efficiently removed by HDL transport.

The transformation of a clinically silent lesion into an atheromatous plaque proceeds by the migration of a variety of cell types, including transformed smooth muscle cells. These cells extend the atheroma by the further oxidation of circulating LDL, the accumulation of lipid and the elaboration of collagen and elastin.

Such antioxidants as probucol and Vitamins E and C have been found to inhibit the oxidation of LDL in vitro and the development of atherosclerotic lesions in experimental animals. The major lipid-soluble antioxidant in LDL is Vitamin E and, in vitro, the addition of Vitamin E to serum extends the lag-phase preceding LDL oxidation. However, data suggest that Vitamin E alone is not sufficient to protect LDL and indicate that a combination of antioxidants, including the carotenoids, provides enhanced protection.

In humans, daily ingestion of 1,200 IU of Vitamin E has been shown to increase the (alpha)-tocopherol content of LDL by up to 215% and to increase the resistance of LDL to oxidation by as much as 175%. Such data are consistent with a large collection of animal studies, cell-culture work and recent epidemiologic studies that show an inverse correlation between the plasma Vitamin E level and mortality from ischemic heart disease.

Thus, there is compelling evidence that dietary antioxidants can directly influence the development of atherosclerosis and from a public health perspective, there is little doubt that a positive effect exists and patient interest is best served by encouraging increased consumption of these dietary factors.

The identification of LDL oxidation as a key event in atherosclerosis indicates that is the risk of atherosclerosis can be reduced by antioxidant supplementation. Vitamin E is the major naturally-occurring antioxidant inhuman lipoproteins. Most circulating carotenoids are associated with lipoproteins in plasma. The largest fraction of total carotenoids is found in LDL, as evidenced by the typically yellow color of this lipoprotein fraction. The largest fraction of hydrocarbon carotenoids (e.g., beta-carotene and lycopene), as well as most Vitamin E and other tocopherols, is transported by LDL suggesting that these compounds in particular may play an important role in preventing oxidative modification of this lipoprotein fraction.

While the invention will now be described in connection with certain preferred embodiments in the following examples of unpublished original studies so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

Thus, the following examples, showing various unexpected and synergistic results, serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

Example 1

The potential of dried beer solids to inhibit degradation (promote stabilization) of L-ascorbic acid in aqueous solution, and to compare the inhibitory effect of several different dried beer solid extracts was assessed. L-ascorbic acid degradation was monitored by determining the quantity of remaining reduced form using HPLC.

Methods

1) Test Samples

Test substances were (1) Heliant extract (Hel), (2) dried beer solids powder obtained by dehydrating whole beer (CG-P), (3) dried beer solids obtained as ethanol extract (CG-E), (4) dried beer solids obtained as methanol extract (CG-M), both as prepared from CG-P, (5) a mixture containing 1 part Heliant and 9 parts CG-E (Hel+CG-E) based on weight (1:9, w/w). Epicatechin (EPC), catechin (CAT) and L-ascorbic acid were obtained from Sigma Chem., Co.

2) HPLC Analysis

The HPLC system used in this study was manufactured by Waters, comprised of the following: two 510 pumps, an automatic sampling device, and photodiode array detector. For the determination of L-ascorbic acid, isocratic analysis was performed with a Nova-pak $C_{18}$ column (Waters) (3.9×150 mm, 5 µparticle size), fitted with a precolumn filled with larger particle size $C_{18}$ resin (30-40µ) positioned ahead of the analytical column. The mobile phase consisted of 3.7 mM $KH_2PO_4$ (pH 4.0), which was delivered at a flow rate of 0.5 ml/min. Absorbance was monitored at 254 nm; peaks areas were determined with Millenium software.

3) Procedure

A 0.01% solution (w/v) of L-ascorbic acid was prepared in 0.1 M acetate buffer, pH 5.3. Test samples were added to yield final concentration of 1 mg/ml, 0.1 mg/ml, or 0.01 mg/ml. These samples were incubated at ambient temperature (~22°C) in transparent glass tubes, in a room illuminated by fluorescent lighting, and the quantity of remaining L-ascorbic acid was periodically determined as described above. Results were expressed as the quantity of L-ascorbic acid remaining (%) with respect to the original amount observed at time zero. Test samples of all dried beer solids samples were dissolved in water, and EPC and CAT were in methanol, and the solvent was added to yield a final concentration of 1.0%.

Results

Figure 1:
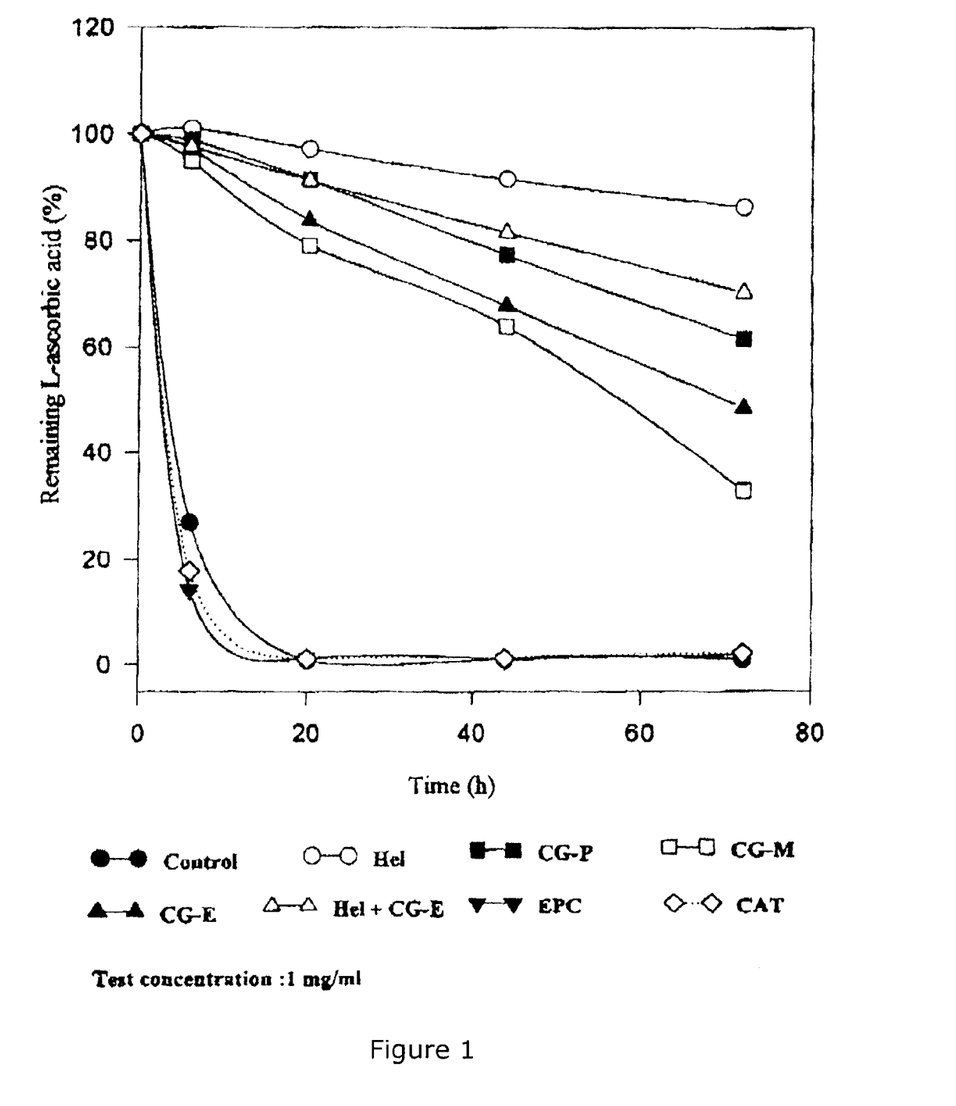
FIG. 1 is a graph showing the effect of various test substances (concentration 1 mg/ml) on L-ascorbic acid degradation.
Figure 2:
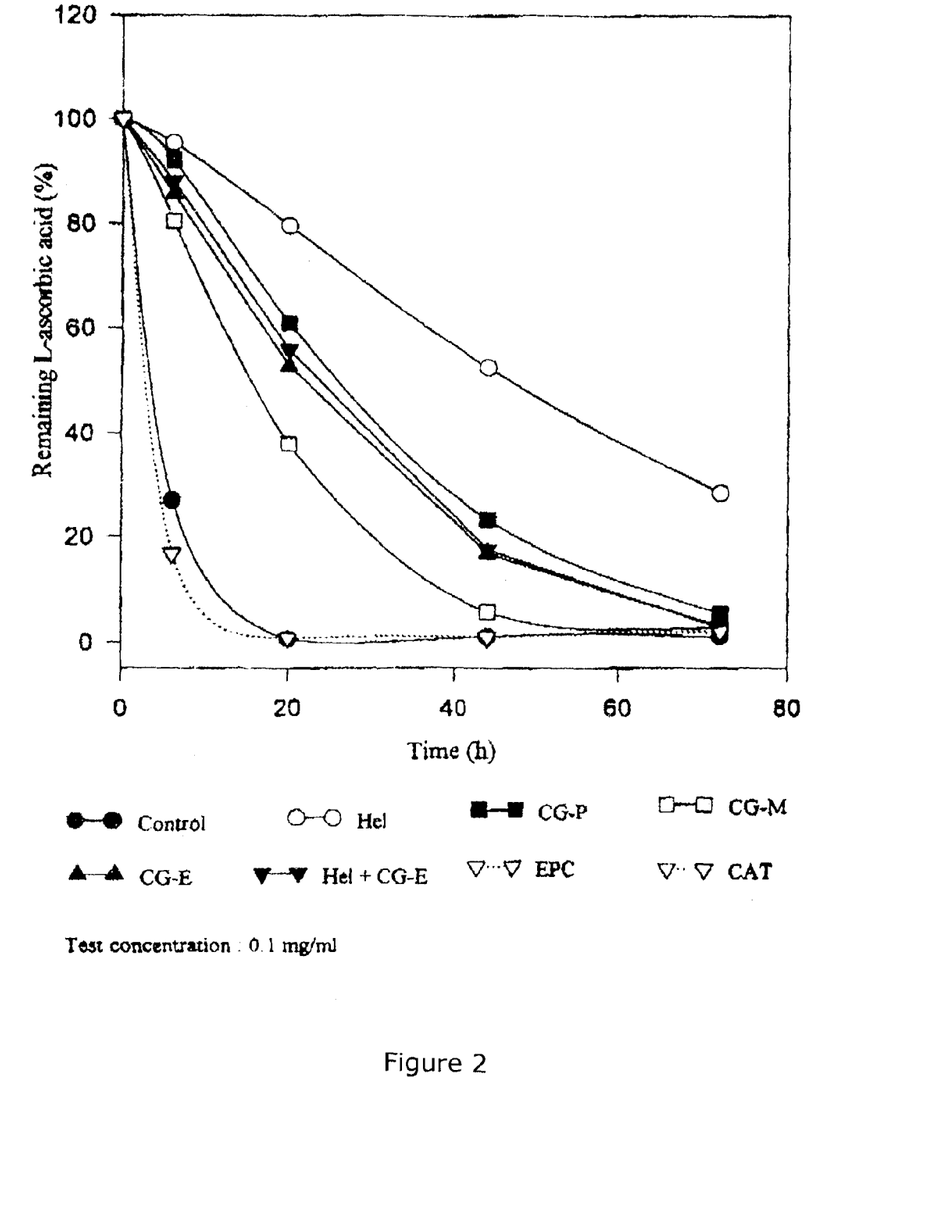
FIG. 2 is a graph showing the effects of various test substances (concentration 0.1 mg/ml) on L-ascorbic acid degradation.
Figure 3:
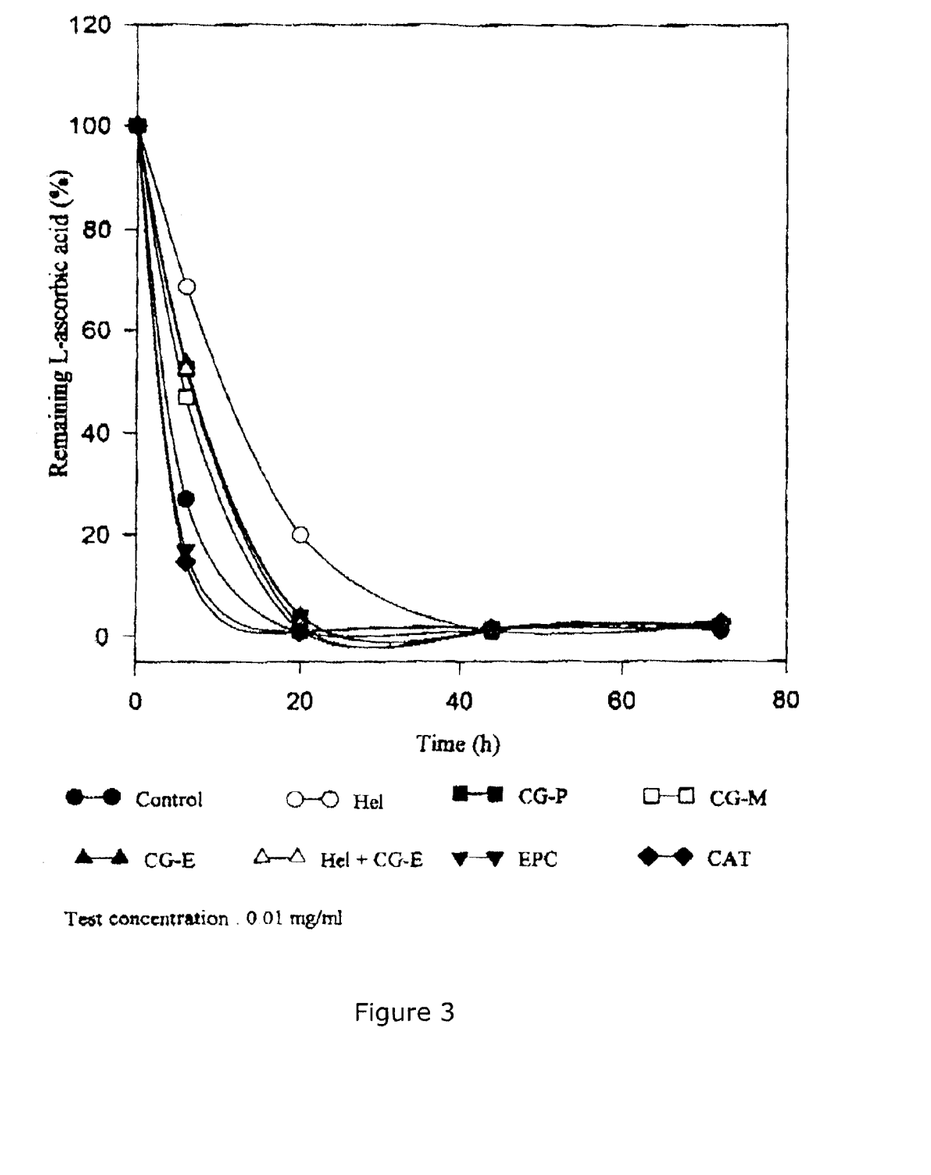
FIG. 3 is a graph showing the effects of various test substances (concentration 0.01 mg/ml) on L-ascorbic acid degradation.

As shown in Table 1 and FIGS. 1-3, each dried beer solids sample and Heliant inhibited L-ascorbic acid degradation. The inhibitory effect was dose-dependent (Table 1). Neither epicatechin (EPC) nor catechin (CAT) showed any inhibitory effects when tested up to a concentration of 1.0 mg/ml (Table 1, FIGS. 1-3). As reported previously, Heliant inhibits the degradation of L-ascorbic acid in aqueous solution. The novel data presented herein show that dried beer solids composition of the present invention are unexpectedly also active in this process. The potency of inhibition was roughly in the following order: Heliant (Hel)>(CG-P)>Heliant and CG-E mixture (Hel+CG-E)>(CG-E)>(CG-M).

TABLE I

Stabilization of Vitamin C by antioxidant formulation.

| Time | Control | concentration (mg/ml) | Hel | CG-P | CG-M | CG-E | Hel + CG-E | EPC | CAT |
|---|---|---|---|---|---|---|---|---|---|
| 0 h | 100 | | 100 | 100 | 100 | 100 | 100 | 100 | 100 |
| 6 h | 26.9 | 1.0 | 101.1 | 98.8 | 94.9 | 97.1 | 97.6 | 14.1 | 17.7 |
| | | 0.1 | 95.4 | 92.1 | 80.5 | 85.7 | 88.2 | 17.0 | 16.7 |
| | | 0.01 | 68.5 | 52.3 | 46.8 | 53.3 | 52.2 | 16.9 | 14.6 |
| 20 h | 0.7 | 1.0 | 97.2 | 91.4 | 79.1 | 83.8 | 91.3 | 1.1 | 1.0 |
| | | 0.1 | 79.6 | 61.1 | 37.9 | 52.8 | 55.9 | 0.8 | 0.8 |
| | | 0.01 | 19.8 | 3.7 | 1.0 | 3.9 | 2.0 | 0.8 | 0.8 |
| 44 h | 1.0 | 1.0 | 91.6 | 77.3 | 64.1 | 67.9 | 81.6 | 0.9 | 1.2 |
| | | 0.1 | 52.6 | 23.2 | 5.7 | 16.8 | 17.5 | 0.8 | 1.0 |
| | | 0.01 | 0.9 | 0.9 | 1.3 | 0.9 | 0.9 | 1.3 | 1.4 |
| 72 h | 1.0 | 1.0 | 86.4 | 61.8 | 33.0 | 48.6 | 70.4 | 1.8 | 2.2 |
| | | 0.1 | 28.4 | 5.4 | 2.8 | 3.1 | 2.9 | 1.9 | 2.0 |
| | | 0.01 | 1.6 | 1.7 | 1.7 | 1.8 | 1.8 | 2.2 | 2.4 |

Hel: Heliant,
CG-P dried beer solid powder,
CG-M: dried beer solid methanol extract
CG-E: dried beer solid ethanol extract
Hel + CG-E: heliant 1 part + CG-E 9 parts
EPC: Epicatechin,
CAT: Catechin Example 2

Figure 4:
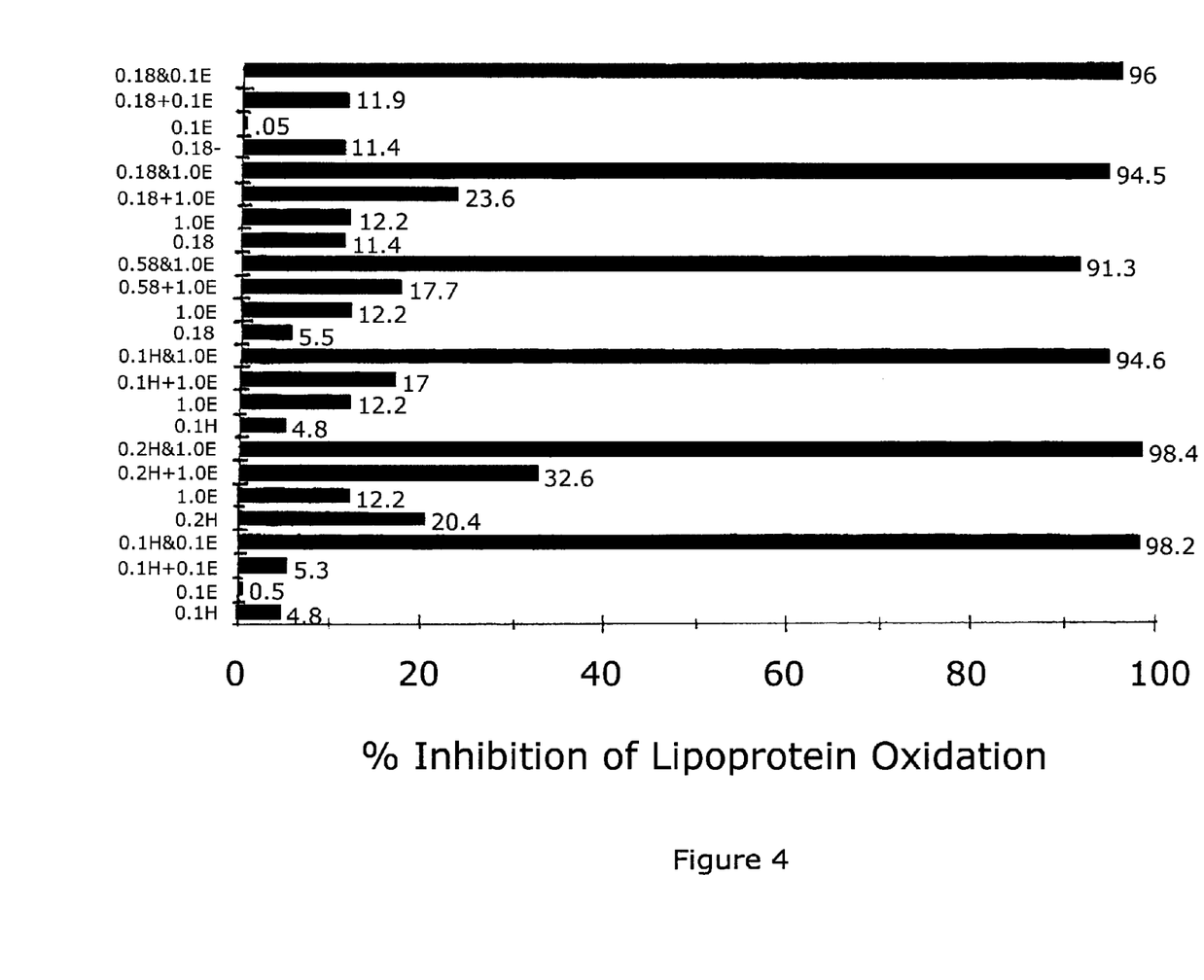
FIG. 4 is a graph showing the synergistic effects of various compounds on the inhibition of lipoprotein oxidation.

Various combinations of antioxidants were studied to determine synergetic effects on lipoprotein oxidation. As shown in FIG. 4, there were unexpected synergisms between the dried beer solids (B), Heliant (H), and Vitamin E (E) in a model which mimics heart disease. The antioxidants were used alone and together at micromolar and submolar concentrations to determine additive and syngistic effects on percentage inhibition of lipoprotein oxidation. A result when used together which is greater than the sum of this effects alone is considered to be a synergistic response. Table 2 shows a similar unexpected synergistic effect on lipoprotein oxidation when the dried beer solids are combined with Vitamin E (α-tocopherol).

Table 3 shows a similar synergistic effect on lipoprotein oxidation when the dried beer solids (DBS) are combined with Heliant (Upper Panel) and Grow C (a natural Vitamin C extract) (Lower Panel). Table 4 shows a similar unexpected synergistic effect on lipoprotein oxidation at one level when dried beer solids are combined with Vitamin C.

TABLE 2

Combined antioxidant effects of dried beer solids and Vitamin E in a heart disease model.

| E (mg) | Inhibition of E Alone (%) | Beer Extract (mg) | Inhibition of Beer Extract Alone (%) | Calculated Inhibition of Beer Extract + E (%) | Experimental Inhibition of Beer Extract + E (%) | Synergism = ((Experimental − Calculated)/Calculated) × 100 (%) |
|---|---|---|---|---|---|---|
| 25.6 | 10.1 | 0.064 | 4.0% | 14.1% | 15.5% | 9.9% |
| 25.6 | 10.1 | 0.32 | 5.0% | 15.1% | 14.8% | −2.0% |
| 25.6 | 10.1 | 0.64 | 6.0% | 16.1% | 49.6% | 208.0% |
| 25.6 | 10.1 | 3.22 | 12.5% | 22.6% | 37.3% | 65.0% |
| 25.6 | 10.1 | 6.44 | 19.0% | 29.1% | 48.4% | 66.3% |
| 25.6 | 10.1 | 16.1 | 36.8% | 46.9% | 98.0% | 91.9% |

TABLE 3

Combined effects of dried beer solids and Heliant (Upper Panel) and Grow C* (Lower Panel) in a heart disease model.

| Weight Ratio DBS:Heliant | % Inhibition DBS Alone | % Inhibition Heliant Alone | % Inhibition of Mixture of DBS and Heliant Calculated | % Inhibition of Mixture of DBS and Heliant Experimental and Synergism |
|---|---|---|---|---|
| 9:1 | 37.5% | 5.5% | 43% | 53.5% positive syn. |
| 5:1 | 38.3% | 32% | 70.3% | 64.8% negative syn. |
| 1:1 | 45.8% | 30.6% | 76.4% | 52.4% negative syn. |

TABLE 3-continued

Combined effects of dried beer solids and Heliant (Upper Panel) and Grow C* (Lower Panel) in a heart disease model.

| | | | | |
|---|---|---|---|---|
| 1:2 | 4.8% | 42.3% | 47.1% | 40.2% negative syn. |
| 1:4 | 3.6% | 47.6% | 51.2% | 39.8% negative syn |

| Weight Ratio Grow C:DBS | % Inhibition DBS Alone | % Inhibition Grow C Alone | % Inhibition of Mixture of DBS and Grow C Calculated | % Inhibition of Mixture of DBS and Grow C experimental and Synergism |
|---|---|---|---|---|
| 0.50:1 | 30.0% | 8.0% | 38.0% | 42.0% positive syn. |
| 0.375:1 | 28.5% | 7.8% | 36.3% | 39.7% positive syn. |
| 0.250:1 | 32.0% | 7.0% | 39.0% | 58.6% positive syn. |
| 0.202:1 | 37.5% | 6.8% | 44.3% | 62.8% positive syn. |
| 0.100:1 | 38.0% | 2.0% | 40.0% | 42.4% additive |

*Natural vitamin C extract.

TABLE 4

Combined effects of dried beer solids and Vitamin C in heart disease model.

| Weight Ratio Vit C:DBS | % Inhibition DBS Alone | % Inhibition Vit C Alone | % Inhibition of Mixture of DBS and Vit C Calculated | % Inhibition of Mixture of DBS and Vit C Experimental |
|---|---|---|---|---|
| 0.680:1 | 30.0% | 3.0% | 33.0% | 32.5% additive |
| 0.520:1 | 28.5% | 2.6% | 31.1% | 31.0% additive |
| 0.343:1 | 32.0% | 2.0% | 34.0% | 35.2% additive |
| 0.274:1 | 37.5% | 1.2% | 38.7% | 43.6% additive |
| 0.136:1 | 38.0% | 0% | 38.0% | 36.2 additive |

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the processes, compositions of matter, means, methods and steps described in the specification. As one of ordinary skill in the art will readily appreciate from the disclosure of the present invention, processes, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, compositions of matter, means, methods, or steps.

What is claimed is:

1. A dietary formulation in solid form comprising:
   dried beer solids having a hops component, with the dried beer solids absent ethanol and water; and
   an antioxidant compound selected from the group consisting of Vitamin C and Vitamin E,
   with the dried beer solids included in the dietary formulation in a concentration of about 10 to 0.1 parts of the dried beer solids to 1 part of Vitamin C and in a concentration of about 0.63 to 0.125 parts of dried beer solids to 1 part Vitamin E.

2. The dietary formulation of claim 1 further comprising D-ribose.

3. The method of mitigating oxidation and glycation of low density lipoproteins in a subject, comprising:
   providing a composition comprising dried beer solids and a phenolic antioxidant; and
   orally administering the composition to the subject, wherein the composition has enhanced activity against oxidation or glycation of LDL-cholesterol.

4. The method of claim 3 wherein the composition further comprises D-ribose.

5. The dietary formulation of claim 1 wherein the dried beer solids are from a beer waste stream.

* * * * *